(12) United States Patent
Redegeld et al.

(10) Patent No.: US 7,056,511 B2
(45) Date of Patent: Jun. 6, 2006

(54) INHIBITION OF PROTEIN BINDING TO MAST CELLS

(75) Inventors: Franciscus Antonius M. Redegeld, Zeist (NL); Aletta Desireé Kraneveld, Nigtevecht (NL); Franciscus Petrus Nijkamp, Houten (NL)

(73) Assignee: Fornix Biosciences N.V., Lelystad (NL)

( * ) Notice: Subject to any disclaimer, the term of this patent is extended or adjusted under 35 U.S.C. 154(b) by 0 days.

(21) Appl. No.: 10/888,552

(22) Filed: Jul. 9, 2004

(65) Prior Publication Data

US 2005/0049183 A1    Mar. 3, 2005

Related U.S. Application Data

(63) Continuation of application No. 09/756,899, filed on Jan. 9, 2001, now abandoned, which is a continuation of application No. PCT/NL99/00430, filed on Jul. 7, 1999.

(30) Foreign Application Priority Data

Jul. 9, 1998    (NL) ..................................... 1009601

(51) Int. Cl.
*A61K 38/04* (2006.01)
*C07K 4/12* (2006.01)

(52) U.S. Cl. .................................... 424/184.1; 530/328
(58) Field of Classification Search ............. 424/184.1; 530/328
See application file for complete search history.

(56) References Cited

U.S. PATENT DOCUMENTS 3,907,502 A    9/1975    Brink
4,654,325 A    3/1987    Selenke
4,977,244 A    12/1990   Muchmore et al.

OTHER PUBLICATIONS

Stryer et al, in Biochemistry, Third edition, W H Freeman Company, New York, pp. 31-33, 1998.*
Gennaro et al., in Remington's Pharmaceutical Sciences, eighteenth edition, 1990, pp. 1300-1329.
Hoppers et al., J. Clinical Immunology, Abstract, Jul. 1989, pp. 338-350, vol. 9, No. 4.
Huang et al., "Localization of a Single Binding Site for Immunoglobulin Light Chains on Human Tamm-Horsfall Glycoprotein", The Journal of Clinical Investigation, vol. 99, No. 4, pp. 732-736, Feb. 1997.
McDonnell et al., Nature Structural Biology, May 1996, pp. 419-426, vol. 3, No. 5.
Ngo et al., 1994, The Protein Folding Problem and Tertiary Structure Prediction, pp. 492-495.
Redegeld et al., Nature Medicine epublication, Jun. 17, 2002.
Rocken et al., Nature Medicine, Jul. 2002, pp. 668-670, vol. 9, No. 7.
Van Noort et al., International Review of Cytology, 1998, pp. 127-206, vol. 178.

* cited by examiner

*Primary Examiner*—Christina Chan
*Assistant Examiner*—Phuong N Huynh
(74) *Attorney, Agent, or Firm*—TraskBritt

(57) ABSTRACT

The invention relates to a compound inhibiting the binding of the free light chain of immunoglobulin (Ig LC) to mast cells. It has been found that Ig LC is the agent responsible for the sensitization of mast cells. The compounds according to the invention can thus be used for the preparation of a drug for the treatment of a disease whose symptom is an elevated Ig LC concentration in serum or spinal fluid. The invention also relates to a method of screening a series of compounds on their ability to reduce the sensitization of mast cells.

4 Claims, 3 Drawing Sheets

INHIBITION OF PROTEIN BINDING TO MAST CELLS

CROSS-REFERENCE TO RELATED APPLICATIONS

Figure 1:
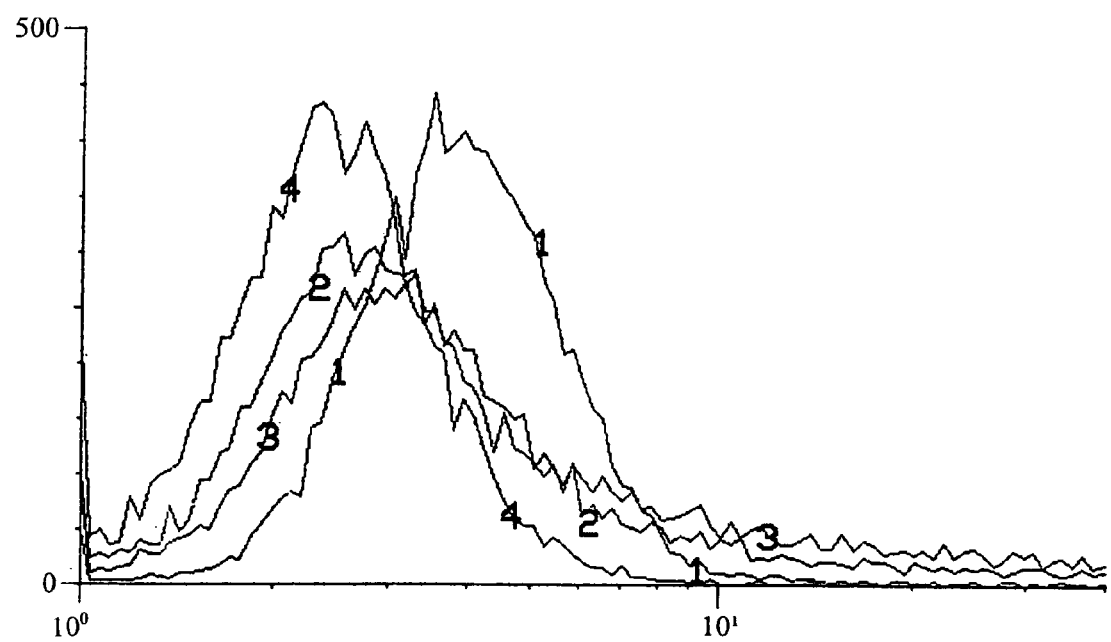

This application is a continuation of U.S. patent application Ser. No. 09/756,899, filed Jan. 9, 2001, abandoned, which application claims priority to, and is a continuation of, International Application No. PCT/NL99/00430, filed on 7 Jul. 1999, designating the United States of America, the contents of which are incorporated by this reference.

TECHNICAL FIELD

The current invention relates generally to biotechnology and the field of immunology and, more specifically, to components which sensitize mast cells.

BACKGROUND OF THE INVENTION

In the field of immunology, Askenase, P. W. et al. (*J. Exp. Med.* 157, p. 862–873 (1983)) describe a "T-cell factor" which sensitizes mast cells. This T-cell factor is a very impure composition. Until now, it was not known which component/components was/were responsible for the sensitization.

DISCLOSURE OF THE INVENTION

Applicants have found that the free light chain of immunoglobulin (Ig LC) is a constituent of the T-cell factor and is the agent responsible for the sensitization of mast cells. It has been found that Ig LC sensitizes the mast cells antigen-specifically.

Therefore, the present invention relates to a compound which inhibits the binding of the free light chain of immunoglobulin to mast cells, wherein the compound, in the presence of an equimolar quantity of free light chain (LC) of immunoglobulin reduces its binding by at least 5%.

Such a compound is of major importance for use as a means for suppressing the unpleasant effects resulting from sensitization experienced by a patient. The compounds can be detected in a simple manner, for example, by incubating a compound to be tested, together with fluorescent labeled Ig LC and mast cells. With the aid of a fluorescence microscope or, for quantitative measurement, a Fluorescence Activated Cell Sorter (FACA), inhibition may be assessed. This inhibition may occur due to competition between the compound and Ig LC for binding to the mast cell.

According to a preferred embodiment, the compound can bind to the free light chain of immunoglobulin, while the compound is capable of competing with a peptide binding to the free light chain having the amino acid sequence AHWSGHCCL (SEQ ID NO:1) and, in the presence of an equimolar quantity of the peptide, the compound reduces its binding by at least 5%.

Huang Z.-Q. et al. (ref. 2) describe a unique urinary protein, Tamm-Horsfall glycoprotein (THP, also known as uromoduline) causing aggregation of immunoglobulin light chains and THP. This aggregate causes renal failure due to clogging of the distal nephron of the kidney. The publication discloses tryptic peptides of THP also causing aggregation. The use thereof or THP as a drug is not disclosed, nor is the binding thereof to mast cells disclosed.

Preferably, the compound reduces the binding of the peptide by at least 10%, preferably by at least 25%, more preferably by at least 50%, even more preferably by at least 75% and most preferably by at least 90%.

In principle, such compounds are very useful as an active component for a pharmaceutical composition, particularly if binding is reduced by more than 50%.

Within the scope of the present invention, the peptide may also be used as the active component. It is also possible to use peptides with unusual and/or modified amino acids. According to a preferred embodiment, the compound is a peptidomimeticum.

A suitable peptidomimeticum is, for example, a peptoid such as a peptoid corresponding with the peptide, but in which the side chains are located on the nitrogen atoms of the peptide backbone. In comparison with the original peptide, such a peptoid has a longer half-life in the blood. The synthesis of peptoids is well documented in the art. The most important difference with the synthesis of peptides is the different starting materials corresponding to the amino acids.

The present invention also relates to a method of screening a series of compounds for their capability to bind the free light chain of immunoglobulin using a labeled compound capable of binding the free light chain of immunoglobulin, and capable of competing with the peptide with the amino acid sequence AHWSGHCCL (SEQ ID NO:1) of the formula sheet, wherein the screening is performed using a test comprising a competition reaction between the compound to be tested and the labeled compound. The test is suitably a homogenous test, making it possible to quickly screen compounds and to select active compounds.

In the present invention, a homogenous test is understood to be a test wherein, for detection, it is not necessary to separate a noncomplexed labeled peptide (or peptidomimeticum) from a complexed-labeled peptide. Instead of the labeled peptide with the amino acid sequence AHWSGHCCL (SEQ ID NO:1), it is, of course, also possible to use a compound found with that peptide.

Two examples of very suitable homogenous tests are based on fluorescence (de)polarization or internal energy transfer respectively, as these allow for optimal use of, respectively, the difference in size between complexed-labeled and noncomplexed-labeled peptides, and the small distance between the fluorophore and chromophore.

The present invention also relates to a method of screening a series of compounds for their capability to reduce the sensitization of mast cells, wherein the screening is performed by incubating a compound to be tested and a labeled free light chain of immunoglobulin with a mast cell, and detecting reduced binding of the labeled free light chain of immunoglobulin.

It is preferred that the screening occur under physiological conditions, as the compound will have to be active when used as a drug under those conditions.

The compound may be used for pharmaceutical purposes, especially if the compound is pharmaceutically acceptable.

Thus the present invention also relates to an application of a compound (obtained) according to the present invention or Tamm-Horsfall glycoprotein (THP) or LC-binding peptide fragments thereof for the preparation of a drug for a disease having as a symptom i) a concentration of the free light chain of immunoglobulin in serum of at least 8 mg/l, in particular of at least 15 mg/l and more in particular 20 mg/l; and/or ii) a concentration of the free light kappa-chain of immunoglobulin in spinal fluid of at least 70 µg/l, in particular at least 100 µg/l, and more in particular 150 µg/l; and/or iii) a concentration of the free lambda-chain of immunoglobulin in spinal fluid of at least 300 µg/l, in particular at least 400 µg/l, and more in particular 500 µg/l.

Important examples of such diseases are asthma, allergy, including contact allergy and occupational allergy, chronic inflammatory bowel disorders, viral infection and multiple sclerosis. Migraine may also be included in the list of disorders.

According to a preferred embodiment, a compound is used which is a peptide or peptidomimeticum with a mass of less than 10 kDal, preferably less than 2 kDal.

If the peptide does not need to be synthesized because it is derived from a protein, the mass is of less importance, although the peptide is then preferably nonimmunogenic.

Thus the present invention also relates to a pharmaceutical composition comprising a compound according to the invention or Tamm-Horsfall glycoprotein (THP) or LC-binding peptides thereof together with a pharmaceutically acceptable carrier or excipient.

Finally, the invention relates to a method of diagnosing a disease in a patient having an elevated level of the free light chain of immunoglobulin in a bodily fluid, wherein a foreign antigen specific for the disease is contacted with the bodily fluid from the patient, and subsequently the presence is determined of a complex of the foreign antigen and the free light chain of immunoglobulin.

The bodily fluid is suitably urine, serum or plasma. Spinal fluid, lung washing and sputum are considered as well. Thus, in the context of the present invention, a bodily fluid also comprises liquids prepared on the basis of the bodily material. The presence of a complex can be detected by using one of many methods known in the state of the art such as a sandwich ELISA wherein the complex is detected using a labeled antibody directed against the free light chain.

Such a labeled antibody is suitably directed against a conserved part of the free light chain.

DETAILED DESCRIPTION OF THE DRAWINGS

Figure 2:
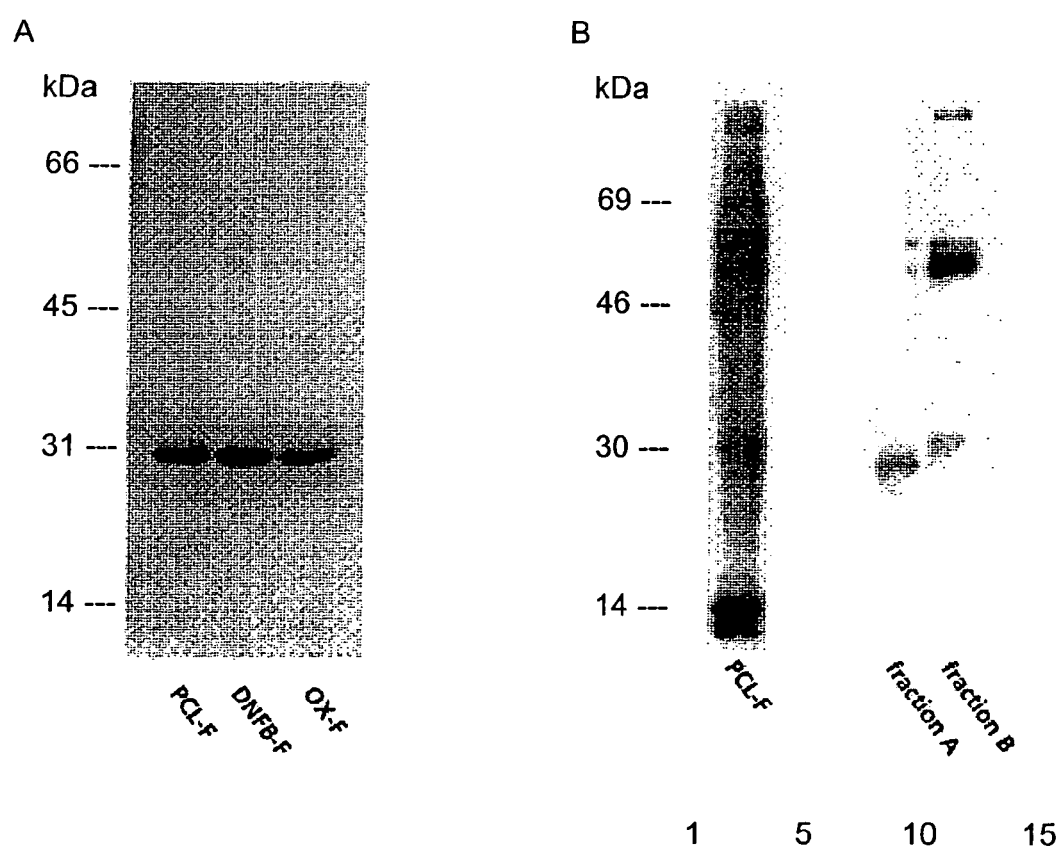
Figure 3:
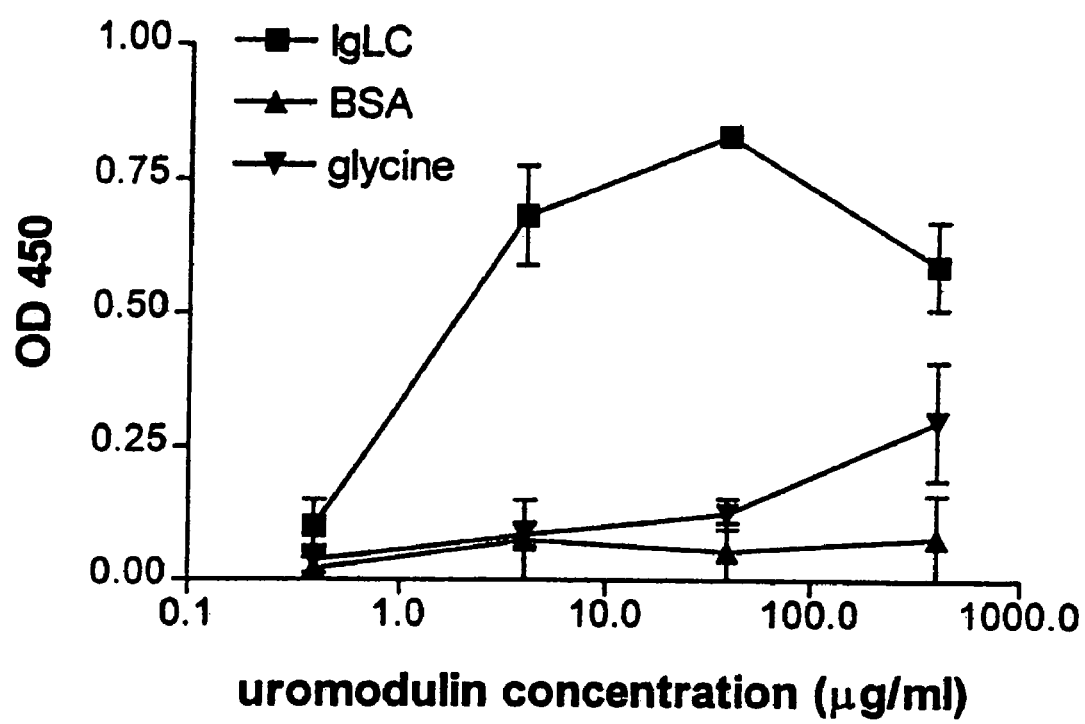

The present invention will now be illustrated by the following examples with reference to the drawings, wherein:

FIG. 1 represents a graph of the relative fluorescence as a measure for the amount of bound Ig LC against the number of mast cells;

FIG. 2, portions A and B, show Western blots after SDS-PAGE electrophoresis; and FIG. 3 shows a graph for an ELISA-based binding assay.

DETAILED DESCRIPTION OF THE INVENTION

Preparation 1: Preparation of Ig LC-Binding Peptide LCBP.

The peptide Ac-AHWSGHCCL-NH$_2$ (SEQ ID NO:1) was prepared using a 430A Applied Biosystems Instruments (Foster City, Calif., U.S.A.) using solid-phase FastMoc chemistry. For the preparation, a Tentagel-S-RAM resin was used as carrier material. Sensitive side chains were protected using His(Trt), Cys(TrT), Trp(boc), Ser(tBu). The peptide was released from the resin and the protective groups were removed using a mixture of trifluoroacetic acid, ethane dithiol and water (95:2.5:2.5 v/v). The raw peptide was precipitated using ether and purified by means of preparative HPILC. The purity of LCBP was verified using analytical HPLC and mass spectrometry.

Preparation 2: Isolation of Lymphocyte Factor

BALB/c mice (RIVM, Bilthoven, the Netherlands) were skin-sensitized using picrylchloride (PLC), dinitrofluorobenzene or oxazolone as described earlier (ref. 1). Four days after sensitization spleen cells ($10 \times 10^6$ cells/ml) were cultured for 24–48 hours in RPMI medium supplemented with penicillin, streptomycin and gentamycin. The supernatant was harvested and antigen-binding proteins were isolated using hapten-affinity chromatography (bovine gamma globulin or BSA provided with hapten immobilized to Affigel-10 (Bio Rad Labs, Veenendaaj, the Netherlands)) as described by Ferguson. T. A. et al. (ref. 3). After washing the column with PBS+ 0.5 M NaCl, the proteins were eluted with 5 ml 5 M guanidine solution. Subsequently, extensive dialysis against PBS took place. Proteins of biologically active samples, such as determined with an ear swelling test (see hereinafter), were fractionated using 15% Tricine SDS-PAGE, blotted onto PVDF and subsequently subjected to an Edman degradation for amino acid sequence analysis.

To determine the presence of kappa Ig LC, the hapten-binding proteins were fractionated using 12.5% SDS-PAGE, blotted onto PVDF and tested with horseradish peroxidase-labeled anti-Ig kappa LC (The Binding Site, Birmingham, U.K.) in a dilution of 1:2000. Immunoreactive proteins were visualized using ECL (Amersham Pharmacia Biotech Benelux, Roosendaal, the Netherlands) according to the manufacturer's recommendations (FIG. 2, portion A). This showed that in lymphocyte factors specific for picric acid, dinitrofluorobenzene and exazolon respectively, the presence of Ig LC could be demonstrated using an anti-kappa Ig LC-specific antibody.

FIG. 2, portion B, shows that the lymphocyte factor comprises a large variety of antigen-binding proteins. The lanes labeled A (eluted with 0.2 MN Na$_2$CO$_3$) and B (void volume of column) are two fractions obtained using affinity chromatography. Of these fractions, only fraction A exhibited the biological activity demonstrated in Example 3. Of the protein with an apparent molecular weight of 27 kDal (p27) DIQMTQSPPSLSAXLG (SEQ ID NO:2), the N-terminal amino acid sequence was determined, which corresponded to the sequence of Ig LC DIQMTQSPSSLSASLG (SEQ ID NO:3) known from the literature.

EXAMPLE 1

Ig LC-Binding to Mast Cells

Basophilic leukemia cells RBL-2H3 (a gift of C. Fewtrell, Ithaca, N.Y., U.S.A.) of the rat, an established model for mast cells, were incubated with 200 ng/$10^5$ cells Ig LC labeled with fluorescein isothiocyanate. They were incubated for 30 minutes at 4° C. in the presence or absence of 250 µg/ml of the peptide LCBP prepared in preparation 1 (peptide binding to the light chain). Subsequently, they were washed using a phosphate-buffered saline supplemented with 1% v/v fetal calf serum and 0.01% w/v sodium azide. Binding of FITC-labeled Ig LC to RBL-2H3 cells was analyzed using a FACScan flow cytometer.

The curve 1 of FIG. 1 shows that the free light chain of Ig binds to mast cells. Secondly, curves 2 and 3 of FIG. 1 show that this binding can be inhibited using LCBP (0.25 mg/ml and 0.50 mg/ml respectively). Curve 4 represents the autofluorescence of unlabeled RBL-2H3 cells.

EXAMPLE 2

Effect of Peptide of LCBP to the Airduct Response

2.1 Sensitization of Mice

Lightly anaesthetized with halothane, mice were passively sensitized by injection with trinitrophenyl (TNP)-specific Ig LC (2 µg in 50 µl of sterile saline) in the retroorbital plexus. Control mice received only 50 µl of sterile saline. Thirty minutes after injection, while being lightly anaesthetized with halothane, all mice received intranasally 50 µl PSA-solution (picrylsulphonic acid dissolved in phosphate-buffered saline).

2.2 Effect of Ig LC and LCBP

A part of each of these two groups of mice simultaneously received 200 µg LCBP (the peptide prepared in Example 1) intranasally.

Bronchoconstriction was measured as described by Kraneveld A. D. et al. (ref. 3) and Zuany-Amorim et al. (ref. 6). In short, five minutes before intranasal application of PSA, mice were placed in a plethysmographic chamber (Buxco Electronics Inc., Shanon, Conn.) in order to analyze respiration and to obtain basal line readings. After the intranasal administration, the animals were directly returned to the chamber. The respiratory resistance was measured for a period of 45 minutes. The respiratory resistance is expressed as a dimensionless value calculated by using the formula for the Penh (ref. 4). For each mouse, the maximum Penh values were measured during an interval of one minute at the moments shown in Table 1.

TABLE 1

| time (min.) | PBS/PBS/PSA (Penh) | PBS/Ig LC/PSA (Penh) | LCBP/PBS/ PSA (Penh) | LcBP/Ig LC/ PSA (Penh) |
|---|---|---|---|---|
| 0[1] | 0.62 ± 0.09 | 0.35 ± 0.03 | 0.44 ± 0.05 | 0.43 ± 0.05 |
| 2.5 | 0.60 ± 0.20 | 1.98 ± 0.16 | 0.60 ± 0.12 | 0.87 ± 0.20 |
| 5 | 0.62 ± 0.20 | 2.29 ± 0.51 | 0.65 ± 0.23 | 1.12 ± 0.20 |
| 7.5 | 0.70 ± 0.30 | 5.29 ± 1.00 | 0.74 ± 0.20 | 0.87 ± 0.10 |
| 10 | 0.60 ± 0.20 | 6.05 ± 1.90 | 0.53 ± 0.03 | 0.87 ± 0.20 |
| 15 | 0.70 ± 0.05 | 3.76 ± 0.70 | 0.49 ± 0.06 | 0.85 ± 0.01 |
| 20 | 0.73 ± 0.20 | 1.88 ± 0.30 | 0.49 ± 0.03 | 0.52 ± 0.05 |

[1]Basal line reading before the challenge

This experiment shows that intranasal administration of LCBP during the passive sensitization (i.v.) with Ig LC can completely inhibit the bronchoconstriction (elevation of Penh) induced by antigen (PSA).

EXAMPLE 3

Effect of Passive Sensitization with Ig LC on Ear Swelling

Mice were, as described by Example 2.1, passively sensitized by injection with a lymphocyte factor PLC-F obtained from a mouse sensitized with picrylchloride or Ig LC specific for trinitrophenyl. Control mice received either only PBS or TNP-specific Ig HC (heavy chain of immunoglobulin). Thirty minutes after injection, picrylchloride (50 µl 0.8% picrylchloride (PCL) dissolved in olive oil) was applied to the ear. After two hours, the thickness of the ear was measured (Table 2).

TABLE 2

| Treatment | Increase in ear thickness ($\times 10^{-5}$ m) |
|---|---|
| PCL-F | 3.94 ± 0.56 |
| TNP-specific Ig LC | 3.77 ± 0.46 |
| PBS* | 0.37 ± 0.40 |
| TNP-specific Ig HC* | 0.01 ± 0.32 |

*Control

This experiment shows that TNP-specific Ig LC has the same effect as lymphocyte factor. The heavy chain does not show this effect.

EXAMPLE 4

Bronchoconstriction with Mast Cell-Deficient Mice

Mast cell-deficient mice (WBB6F1 W/Wv) (Jackson Labs, Bar Harbor, Me., USA) belong to a strain of mice lacking mast cells. Their response to challenge with picrylsulphonic acid 30 minutes after sensitization with PBS (vehicle), LC and IgE (5 micrograms in 50 microliters each) was compared with the response of strain WBB6F1+/+ (Jackson Labs, Bar Harbor, Me., USA) mice having a similar genetic make-up but not mast cell-deficient. Picrylsulphonic acid (50 microliters, 0.6% (w/v)) was administered intranasally and the Penh values were obtained as described in Example 2. The results are given in Table 3.

TABLE 3

| | PBS | | LC | | IgE | |
|---|---|---|---|---|---|---|
| | Mast cell-deficient animals | | | | | |
| Time (min.) | mean | | mean | | mean | |
| 0 | 0.88 | (0.11) | 0.72 | (0.10) | 0.84 | (0.10) |
| 2.5 | 1.15 | (0.44) | 0.82 | (0.23) | 1.84 | (0.60) |
| 5 | 1.15 | (0.17) | 1.01 | (0.16) | 1.96 | (0.48) |
| 7.5 | 1.37 | (0.35) | 1.24 | (0.41) | 2.51 | (0.68) |
| 10 | 1.22 | (0.36) | 1.07 | (0.18) | 2.02 | (0.89) |
| 15 | 1.22 | (0.16) | 1.10 | (0.28) | 1.64 | (0.29) |
| 20 | 0.82 | (0.12) | 0.85 | (0.19) | 1.21 | (0.26) |
| | | | control | | | |
| 0 | 0.72 | (0.04) | 0.98 | (0.12) | 0.95 | (0.21) |
| 2.5 | 1.02 | (0.22) | 2.46 | (0.51) | 2.17 | (0.44) |
| 5 | 1.25 | (0.22) | 6.14 | (1.87) | 4.34 | (1.97) |
| 7.5 | 1.05 | (0.23) | 8.17 | (1.10) | 4.73 | (1.32) |
| 10 | 1.33 | (0.15) | 8.89 | (1.95) | 6.83 | (1.22) |
| 15 | 1.17 | (0.19) | 4.41 | (1.30) | 3.97 | (0.86) |
| 20 | 0.98 | (0.20) | 2.58 | (0.65) | 2.04 | (0.43) |

The standard error (SE) is shown between parentheses.

From this table it can be seen that the mast cell-deficient mice are not sensitized by LC.

EXAMPLE 5

ELISA-Based Binding Assay

Wells of a microtiter plate were coated at room temperature overnight with 2 µg/ml immunoglobulin light chains or, as a first control, Bovine Serum Albumin (BSA). Also, as a second control, wells were treated with 250 mM glycine buffer, pH=9.5. The wells were emptied and washed five times with 0.05% Tween-20 in PBS. The wells were blocked with HPE-buffer (High Performance Elisa buffer, CLB, Amsterdam, The Netherlands) for one hour, and subsequently the wells were washed again with 0.05% Tween-20 in PBS. Human uromodulin was diluted in HPE-buffer and incubated for two hours. The wells were washed five times with 0.05% Tween-20 in PBS.

To detect bound uromodulin, 1/5000 diluted rabbit anti-human uromodulin antiserum was added (Anawa Trading, Zürich, Switzerland) and incubated for one hour. After washing five times with PBS, 0.05% Tween-20 anti-rabbit-IgG conjugated to horse radish peroxidase (CLB) was added and incubated for one hour. Bound peroxidase was detected as is well known in the art using 3, 5, 3', 5'-tetramethyl-benzidine/$H_2O_2$ in 0.11 M sodium acetate pH 5.5. The reaction was stopped using an equal volume of 2 M $H_2SO_4$ and the absorbance was read at 450 nm. The data obtained are depicted in FIG. 3 which shows that a uromodulin concentration within, for example, 4–40 µg/ml, is an excellent concentration for repeating the above ELISA to detect novel compounds according to the present invention. To this end, uromodulin and the compound (preferably at several concentrations) to be investigated are incubated simultaneously in order to compete with each other.

REFERENCES

1. Askenase, P. W. et al. *J. Exp. Med.* 157: p. 862 (1983).
2. Huang, Z.-Q. et al. *J. Clin. Invest.* 99: p. 732 (1997).
3. Kraneveld A. D. et al. Immunol Let. 56, p. 181 (1997).
4. Hamelmann, E., et al., Am. J. Respir. Crit. Care Med. 156, 766–775, (1997).
5. Ferguson, T. A. et al., J. Immunol. 136, 2896–2903, (1986).
6. Zuany-Amorim, C. et al. Science 280, p. 1265–1267 (1998).

---

What is claimed is:

1. A method for reducing the sensitivity of mast cells, said method comprising:

contacting said cells with a free light chain of immunoglobulin-binding peptide (LC-binding peptide) consisting of the peptide of SEQ ID NO:1.

2. The method of claim 1, wherein the LC-binding peptide has a mass of less than 10 kDal.

3. The method of claim 1, wherein the LC-binding peptide has a mass of less than 2 kDal.

4. The method of claim 1, wherein the amount of LC-binding peptide comprises 200 micrograms.

* * * * *

SEQUENCE LISTING

<160> NUMBER OF SEQ ID NOS: 3

<210> SEQ ID NO 1
<211> LENGTH: 9
<212> TYPE: PRT
<213> ORGANISM: Unknown
<220> FEATURE:
<223> OTHER INFORMATION: peptide

<400> SEQUENCE: 1

Ala His Trp Ser Gly His Cys Cys Leu
1               5

<210> SEQ ID NO 2
<211> LENGTH: 16
<212> TYPE: PRT
<213> ORGANISM: Unknown
<220> FEATURE:
<223> OTHER INFORMATION: protein with apparent molecular weight of
      27kDal
<220> FEATURE:
<221> NAME/KEY: misc_feature
<222> LOCATION: (1)..(16)
<223> OTHER INFORMATION: Xaa can be any amino acid

<400> SEQUENCE: 2

Asp Ile Gln Met Thr Gln Ser Pro Pro Ser Leu Ser Ala Xaa Leu Gly
1               5                   10                  15

<210> SEQ ID NO 3
<211> LENGTH: 16
<212> TYPE: PRT
<213> ORGANISM: Unknown
<220> FEATURE:
<223> OTHER INFORMATION: N-terminal amino acid sequence

<400> SEQUENCE: 3

Asp Ile Gln Met Thr Gln Ser Pro Ser Ser Leu Ser Ala Ser Leu Gly
1               5                   10                  15